United States Patent [19]
Jago et al.

[11] Patent Number: 6,117,081
[45] Date of Patent: Sep. 12, 2000

[54] METHOD FOR CORRECTING BLURRING OF SPATIALLY COMPOUNDED ULTRASONIC DIAGNOSTIC IMAGES

[75] Inventors: James R. Jago, Seattle; Robert R. Entrekin, Kirkland, both of Wash.

[73] Assignee: ATL Ultrasound, Inc., Bothell, Wash.

[21] Appl. No.: 09/335,060

[22] Filed: Jun. 17, 1999

Related U.S. Application Data

[60] Provisional application No. 60/102,923, Oct. 1, 1998.

[51] Int. Cl.⁷ ........................................... A61B 8/00
[52] U.S. Cl. ............................................. 600/443
[58] Field of Search .................... 600/437, 443, 600/447, 454–456; 73/625–626

[56] References Cited

U.S. PATENT DOCUMENTS

| | | |
|---|---|---|
| 4,070,905 | 1/1978 | Kossoff . |
| 4,159,462 | 6/1979 | Rocha et al. . |
| 4,649,927 | 3/1987 | Fehr et al. ............................. 600/443 |
| 4,751,846 | 6/1988 | Dousse et al. ......................... 73/602 |
| 5,359,513 | 10/1994 | Kano et al. . |
| 5,479,926 | 1/1996 | Ustuner et al. ........................ 600/440 |
| 5,538,004 | 7/1996 | Bamber ................................ 128/916 |
| 5,566,674 | 10/1996 | Weng ................................... 600/443 |
| 5,575,286 | 11/1996 | Weng et al. ........................... 600/444 |
| 5,655,535 | 8/1997 | Friemel et al. ........................ 600/444 |
| 5,734,738 | 3/1998 | Sato et al. ............................ 600/437 |
| 5,776,066 | 7/1998 | Nock et al. ........................... 600/443 |
| 5,782,766 | 7/1998 | Weng et al. ........................... 600/443 |
| 5,885,218 | 3/1999 | Teo et al. ............................. 600/443 |
| 5,908,390 | 6/1999 | Matsushima . |
| 6,014,473 | 1/2000 | Hossack et al. ....................... 600/443 |

FOREIGN PATENT DOCUMENTS

WO 98 40760 9/1998 WIPO .

OTHER PUBLICATIONS

Feigenbaum, Echocardiography, Lea & Febiger, 1976 at pp 32–34, Philadelphia, PA.

Carpenter et al., Technical Note—A Multimode Real Time Scanner, Ultrsound in Med. & Biol., vol. 6, pp 279–284, Pergamon Press Ltd. 1980, Great Britain.

Berson et al., Compound Scanning With a Electrically Steered Beam, Ultrasonic Imaging 3, pp 303–308, Academic Press, Inc. 1981.

Shattuck et al., Compound Scanning With a Phased Array, Ultrasonic Imaging 4, pp 93–107, Academic Press, Inc. 1982.

Jesperson et al., Multi–Angle Compound Imaging, Ultrasonic Imaging 20, pp 81–102, Dynamedia, Inc. 1998.

Moskalik A. et al., "Registration of Three–Dimensional Compound Ultrasound Scans of the Breast for Refraction and Motion Correction," Ultrasound in Medicine and Biology, U.S., New York, NY, vol. 21, No. 6, pp 769–778.

Elad M. et al., "Restoration of a Single Superresolution Image from Several Blurred, Noisy, and Undersampled Measured Images," IEEE Transactions on Image Processing, U.S. IEEE Inc., New York, vol. 6, No. 12, pp 1646–1658.

*Primary Examiner*—Francis J. Jaworski
*Attorney, Agent, or Firm*—W. Brinton Yorks, Jr.

[57] ABSTRACT

An ultrasonic imaging method is described in which component ultrasonic images which are to be spatially compounded are corrected for misregistration prior to compounding. The component images may be registered to a reference image or registered to form intermediate compound images which are then registered and compounded. The misregistration may be sensed by calculating a similarity or difference metric for a region of interest of the image frames being registered, or on the basis of reference lines acquired for the purpose of registering images.

19 Claims, 8 Drawing Sheets

METHOD FOR CORRECTING BLURRING OF SPATIALLY COMPOUNDED ULTRASONIC DIAGNOSTIC IMAGES

This application claims the benefit of Provisional U.S. patent application Ser. No. 60/102,923, filed Oct. 1, 1998. This application is being concurrently filed with U.S. application Ser. No. [ATL-195] entitled "ULTRASONIC DIAGNOSTIC IMAGING SYSTEM WITH BLURRING CORRECTED SPATIAL COMPOUNDING."

This invention relates to ultrasonic diagnostic imaging systems and, in particular, to ultrasonic diagnostic imaging systems which produce spatially compounded images which are corrected for image blurring.

Spatial compounding is an imaging technique in which a number of ultrasound images of a given target that have been obtained from multiple vantage points or angles are combined into a single compounded image by combining the data received from each point in the compound image target which has been received from each angle. Examples of spatial compounding may be found in U.S. Pat. Nos. 4,649,927; 4,319,489; and 4,159,462. Real time spatial compound imaging is performed by rapidly acquiring a series of partially overlapping component image frames from substantially independent spatial directions, utilizing an array transducer to implement electronic beam steering and/or electronic translation of the component frames. The component frames are combined into a compound image by summation, averaging, peak detection, or other combinational means. The acquisition sequence and formation of compound images are repeated continuously at a rate limited by the acquisition frame rate, that is, the time required to acquire the full complement of scanlines over the selected width and depth of imaging.

The compounded image typically shows lower speckle and better specular reflector delineation than conventional ultrasound images from a single viewpoint. Speckle is reduced (i.e. speckle signal to noise ratio is improved) by the square root of N in a compound image with N component frames, provided that the component frames used to create the compound image are substantially independent and are averaged. Several criteria can be used to determine the degree of independence of the component frames (see, e.g., O'Donnell et al. in IEEE Trans. UFFC v.35, no.4,pp 470–76 (1988)). In practice, for spatial compound imaging with a steered linear array, this implies a minimum steering angle between component frames. This minimum angle is typically on the order of several degrees.

The second way that spatial compound scanning improves image quality is by improving the acquisition of specular interfaces. For example, a curved bone-soft tissue interface produces a strong echo when the ultrasound beam is exactly perpendicular to the interface, and a very weak echo when the beam is only a few degrees off perpendicular. These interfaces are often curved, and with conventional scanning only a small portion of the interface is visible. Spatial compound scanning acquires views of the interface from many different angles, making the curved interface visible and continuous over a larger field of view. Greater angular diversity generally improves the continuity of specular targets. However, the angular diversity available is limited by the acceptance angle of the transducer array elements. The acceptance angle depends on the transducer array element pitch, frequency, and construction methods.

The challenges of acquiring images which are in spatial alignment, or of spatially aligning separate images after they have been received, can be considerable. When the objective is to produce spatially compounded images in real time, an even greater challenge is presented. Image processing must be fast and efficient so that the frame rate of compound images appears to be in real time. The compound images can suffer from motion artifacts, as organs such as the heart and blood vessels can be continually moving as the image data to be compounded is acquired.

One of the problems associated with real time spatial compound imaging is that several image acquisitions are needed to produce each new compound image frame. The time needed to acquire a spatial compound image consisting of N component frames is approximately N times longer than that of each individual component frame. It is generally desirable to acquire a large number of component frames to maximize the image quality of the compound image. However, since the images to be compounded are acquired temporally, the compounding of the images can produce a blurred resultant image. Image blurring occurs in real time spatial compound imaging because common features in the acquired component frames do not superimpose exactly when compounded. Misregistration between acquisition frames can occur for a number of reasons, such as:

1) features can shift position within the image plane due to scanhead and/or patient movement during acquisition (in-plane motion misregistration). This kind of misregistration can be global (translation and/or rotation of entire image) or local (image distortion due to cardiac or respiratory motion, or compression of the tissue with the scanhead).

2) features can shift position due to an incorrect assumption regarding the speed of sound, causing the features to be rendered with axial and angular misregistration (SOS misregistration). This kind of misregistration can be due to an incorrect mean speed of sound or variations in local speed of sound within different tissue types.

Accordingly, it is desirable to prevent blurring from causes such as these when compounding images for real time display.

In accordance with the principles of the present invention, blurring of a compound image is reduced and image quality improved through correction of misregistration errors by registering the component frames to each other prior to compounding. This is possible by the application of image registration techniques. Image registration is meant here as a general term to describe any process which estimates global and/or local displacement information between two images, and warps one (or both) images to make them congruent with each other. A number of techniques may be used to estimate the displacement, including cross correlation search, block matching algorithms, maximum brightness, and feature extraction and tracking. Warping algorithms may be first order, global transformations (translation and/or rotation) or higher order (complex local warping), based on the nature and magnitude of the displacements. The component frames are registered to each other prior to compounding, improving image quality.

Figure 1:
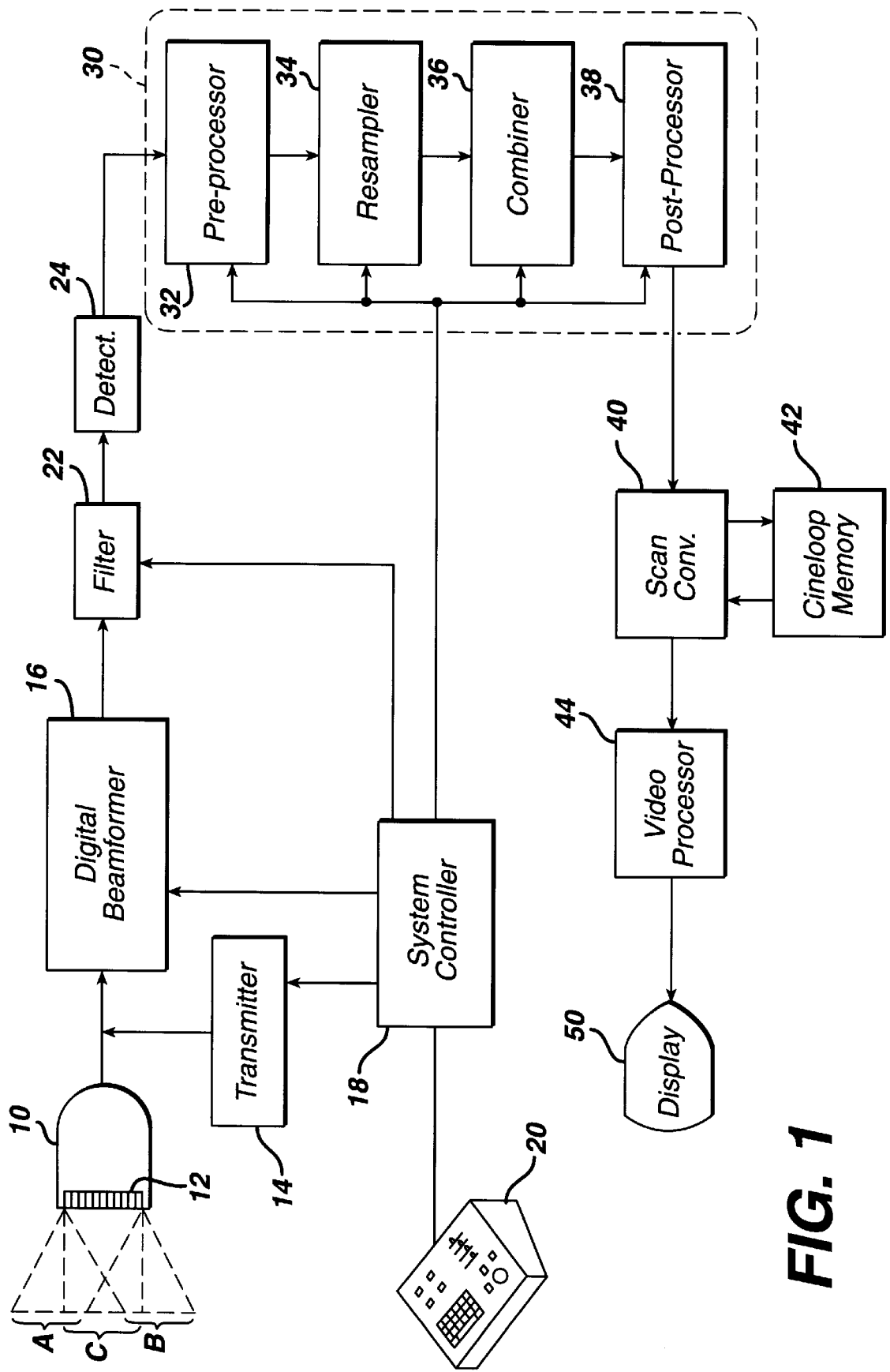
FIG. 1 illustrates in block diagram form an ultrasonic diagnostic imaging system constructed in accordance with the principles of the present invention.

Referring first to FIG. 1, an ultrasonic diagnostic imaging system constructed in accordance with the principles of the present invention is shown. A scanhead 10 including an array transducer 12 transmits beams at different angles over an image field denoted by the dashed rectangle and parallelograms. Three groups of scanlines are indicated in the drawing, labeled A, B, and C with each group being steered at a different angle relative to the scanhead. The transmission of the beams is controlled by a transmitter 14 which controls the phasing and time of actuation of each of the elements of the array transducer so as to transmit each beam from a predetermined origin along the array and at a predetermined angle. The echoes returned from along each scanline are received by the elements of the array, digitized as by analog to digital conversion, and coupled to a digital beamformer 16. The digital beamformer delays and sums the echoes from the array elements to form a sequence of focused, coherent digital echo samples along each scanline. The transmitter 14 and beamformer 16 are operated under control of a system controller 18, which in turn is responsive to the settings of controls on a user interface 20 operated by the user of the ultrasound system. The system controller controls the transmitter to transmit the desired number of scanline groups at the desired angles, transmit energies and frequencies. The system controller also controls the digital beamformer to properly delay and combine the received echo signals for the apertures and image depths used.

The scanline echo signals are filtered by a programmable digital filter 22, which defines the band of frequencies of interest. When imaging harmonic contrast agents or performing tissue harmonic imaging the passband of the filter 22 is set to pass harmonics of the transmit band. The filtered signals are then detected by a detector 24. In a preferred embodiment the filter and detector include multiple filters and detectors so that the received signals may be separated into multiple passbands, individually detected and recombined to reduce image speckle by frequency compounding. For B mode imaging the detector 24 will perform amplitude detection of the echo signal envelope. For Doppler imaging ensembles of echoes are assembled for each point in the image and are Doppler processed to estimate the Doppler shift or Doppler power intensity.

In accordance with the principles of the present invention the digital echo signals are processed by spatial compounding in a processor 30. The digital echo signals are initially pre-processed by a preprocessor 32. The pre-processor 32 can preweight the signal samples if desired with a weighting factor. The samples can be preweighted with a weighting factor that is a function of the number of component frames used to form a particular compound image. The pre-processor can also weight edge lines that are at the edge of one overlapping image so as to smooth the transitions where the number of samples or images which are compounded changes. The pre-processed signal samples may then undergo a resampling in a resampler 34. The resampler 34 can spatially realign the estimates of one component frame or to the pixels of the display space. This may be desirable when there is motion between image frames, there is motion within an image, or there is scanhead motion during image acquisition.

After resampling the image frames are compounded by a combiner 36. Combining may comprise summation, averaging, peak detection, or other combinational means. The samples being combined may also be weighted prior to combining in this step of the process. Finally, post-processing is performed by a post-processor 38. The post-processor normalizes the combined values to a display range of values. Post-processing can be most easily implemented by look-up tables and can simultaneously perform compression and mapping of the range of compounded values to a range of values suitable for display of the compounded image.

The compounding process may be performed in estimate data space or in display pixel space. In a preferred embodiment scan conversion is done following the compounding process by a scan converter 40. The compound images may be stored in a Cineloop® memory 42 in either estimate or display pixel form. If stored in estimate form the images may be scan converted when replayed from the Cineloop memory for display. The scan converter and Cineloop memory may also be used to render three dimensional presentations of the spatially compounded images as described in U.S. Pat. Nos. 5,485,842 and 5,860,924. Following scan conversion the spatially compounded images are processed for display by a video processor 44 and displayed on an image display 50.

Figure 2:
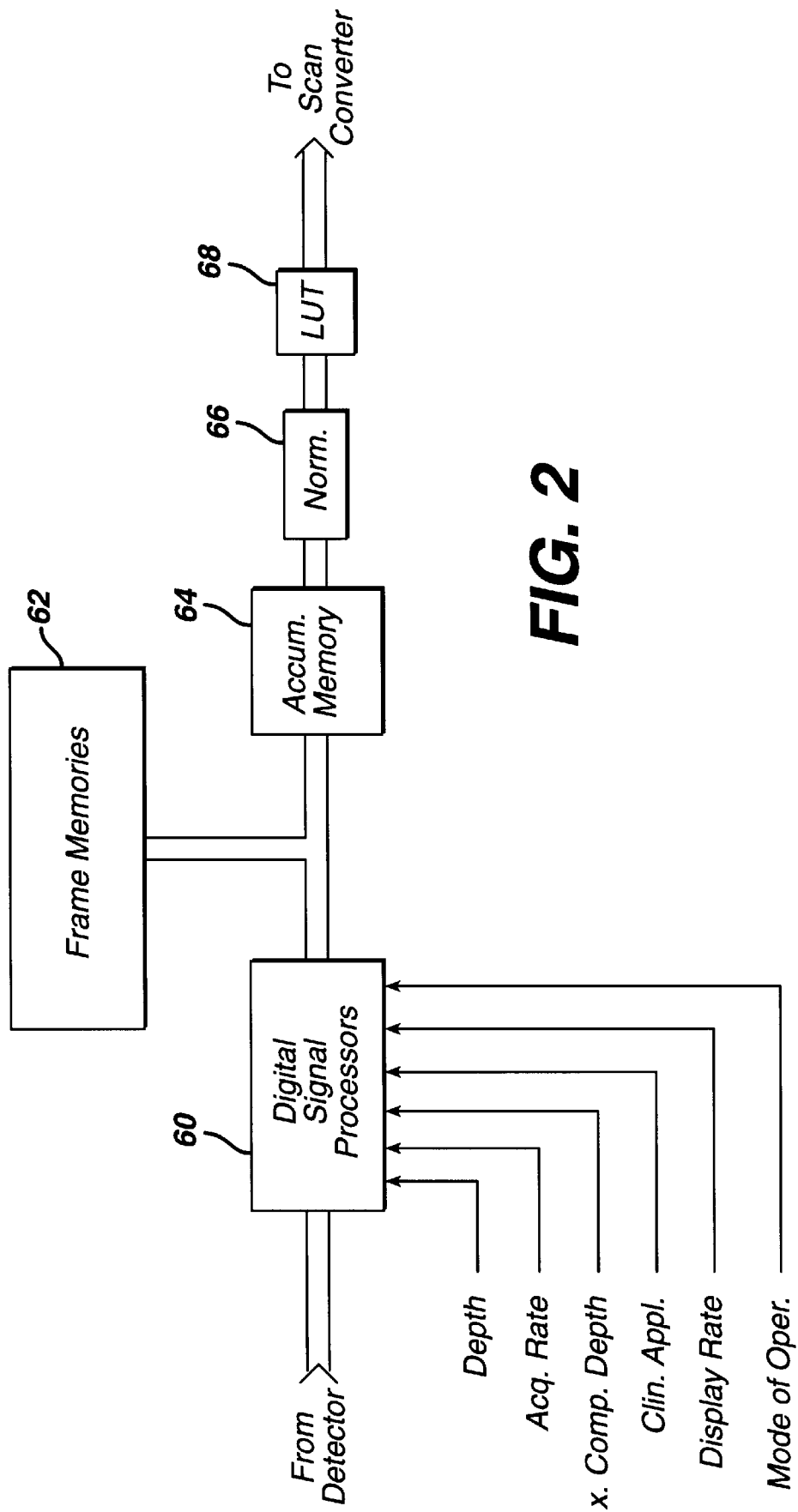
FIG. 2 illustrates in block diagram form a preferred implementation of the spatial compounding processor of FIG. 1.

FIG. 2 illustrates a preferred implementation of the spatial compounding processor 30 of FIG. 1. The processor 30 is preferably implemented by one or more digital signal processors 60 which process the image data in various ways. The digital signal processors 60 can weight the received image data and can resample the image data to spatially align pixels from frame to frame, for instance. The digital signal processors 60 direct the processed image frames to a plurality of frame memories 62 which buffer the individual image frames. The number of image frames capable of being stored by the frame memories 62 is preferably at least equal to the maximum number of image frames to be compounded such as sixteen frames. In accordance with the principles of the present invention, the digital signal processors are responsive to control parameters including image display depth, depth of region of greatest compounding, clinical application, compound display rate, mode of operation, and acquisition rate for determining the number of images to compound at a given instant in time. The digital signal processors select component frames stored in the frame memories 62 for assembly as a compound image in accumulator memory 64. The compounded image formed in the accumulator memory 64 is weighted or mapped by a normalization circuit 66, then compressed to the desired number of display bits and, if desired, remapped by a lookup table (LUT) 68. The fully processed compounded image is then transmitted to the scan converter for formatting and display.

In accordance with the principles of the present invention, the image data of the component frames used to form a compound image is resampled to spatially register the component frames prior to compounding, thereby improving image quality by reducing blurring effects of overlapping unregistered image data. The resampling and registration of component image frames is performed by the programming of the digital signal processors 60, which operate upon component images stored in the frame memories 62. The final registered and compounded image is then stored in the accumulator memory 64. Prior art techniques have used image registration methods for estimating intrinsic tissue properties, such as speed of sound or elasticity, as diagnostic parameters (e.g., Robinson et. al. in *Ult. in Med. & Biol.*, v.17, no.6, pp 633–46 (1991) and Ophir et al. in *Euro. J. Ult.*, v.3, pp 49–70 (1996)), or for estimating scanhead motion to produce a static "panoramic" image (e.g., U.S. Pat. No. 5,566,674).

Figure 3:
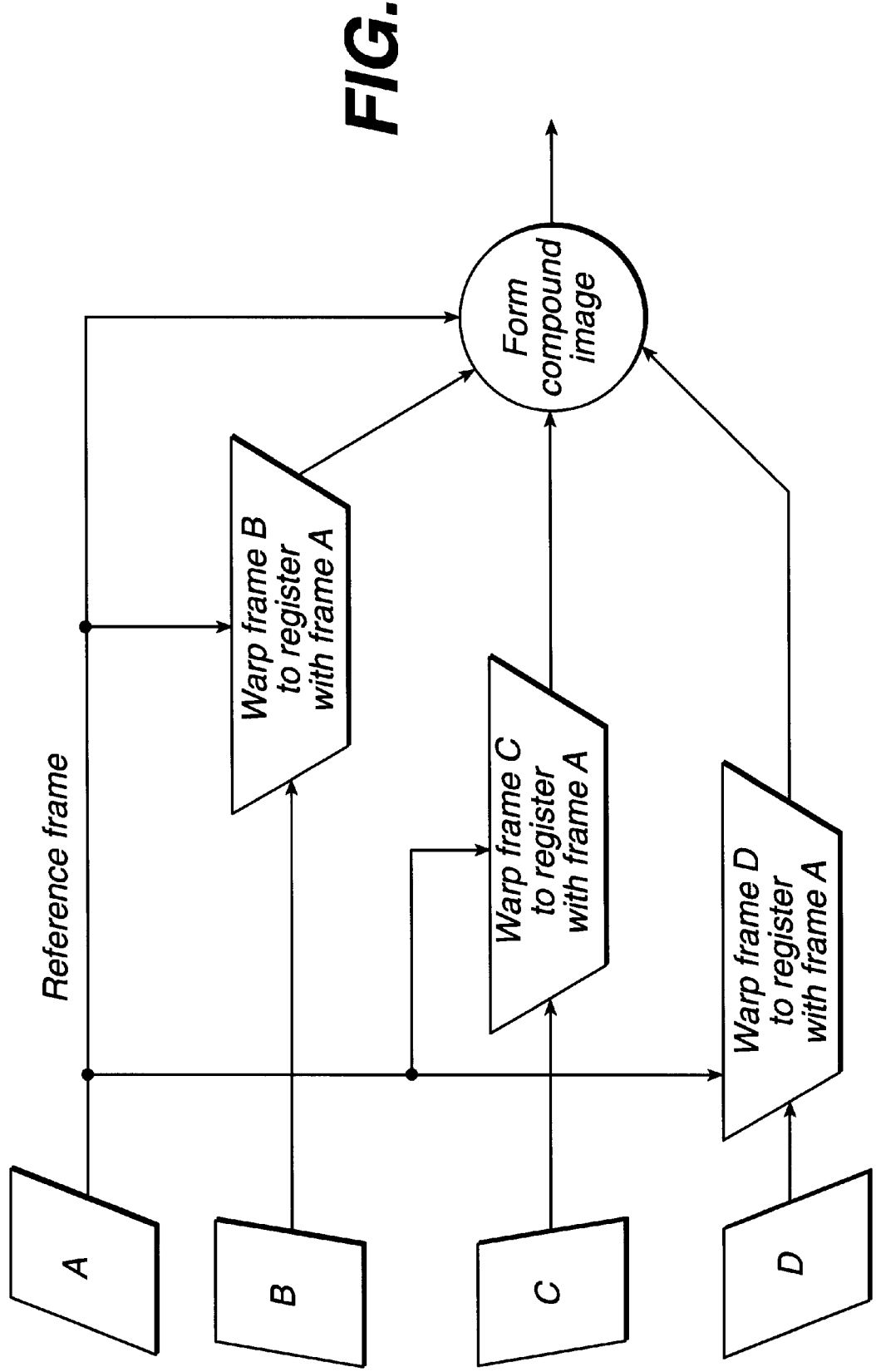
FIG. 3 illustrates a flowchart for registering all of the constituent frames of a compound image to one reference frame.

There are many possible implementations for image registration prior to compounding in accordance with the present invention. FIG. 3 illustrates one embodiment, the "reference frame" method, as applied to a four frame acquisition sequence. The four constituent frames for compounding are shown as A, B, C, and D in temporal sequence in FIG. 3. One of the component frames (A) is designated as the "reference frame," and as subsequent frames (B,C,D) are acquired, they are warped so that their features are congruent with corresponding features of frame A. As the flowchart shows, when frame B is acquired it is registered with frame A, then frame C is acquired and registered with frame A, then frame B is acquired and registered with frame A. After all four constituent frames have been acquired and registered, the aligned frames are compounded. The process is repeated with each new acquisition sequence (E,F,G,H with E designated as the new reference frame). Alternatively, the reference frame can be updated with each new acquisition frame (B, C, D, E with B as the reference frame; C,D,E,F with C as the reference frame; etc.) Any one of the frames of each four frame sequence may de designated as the reference frame.

Figure 4:
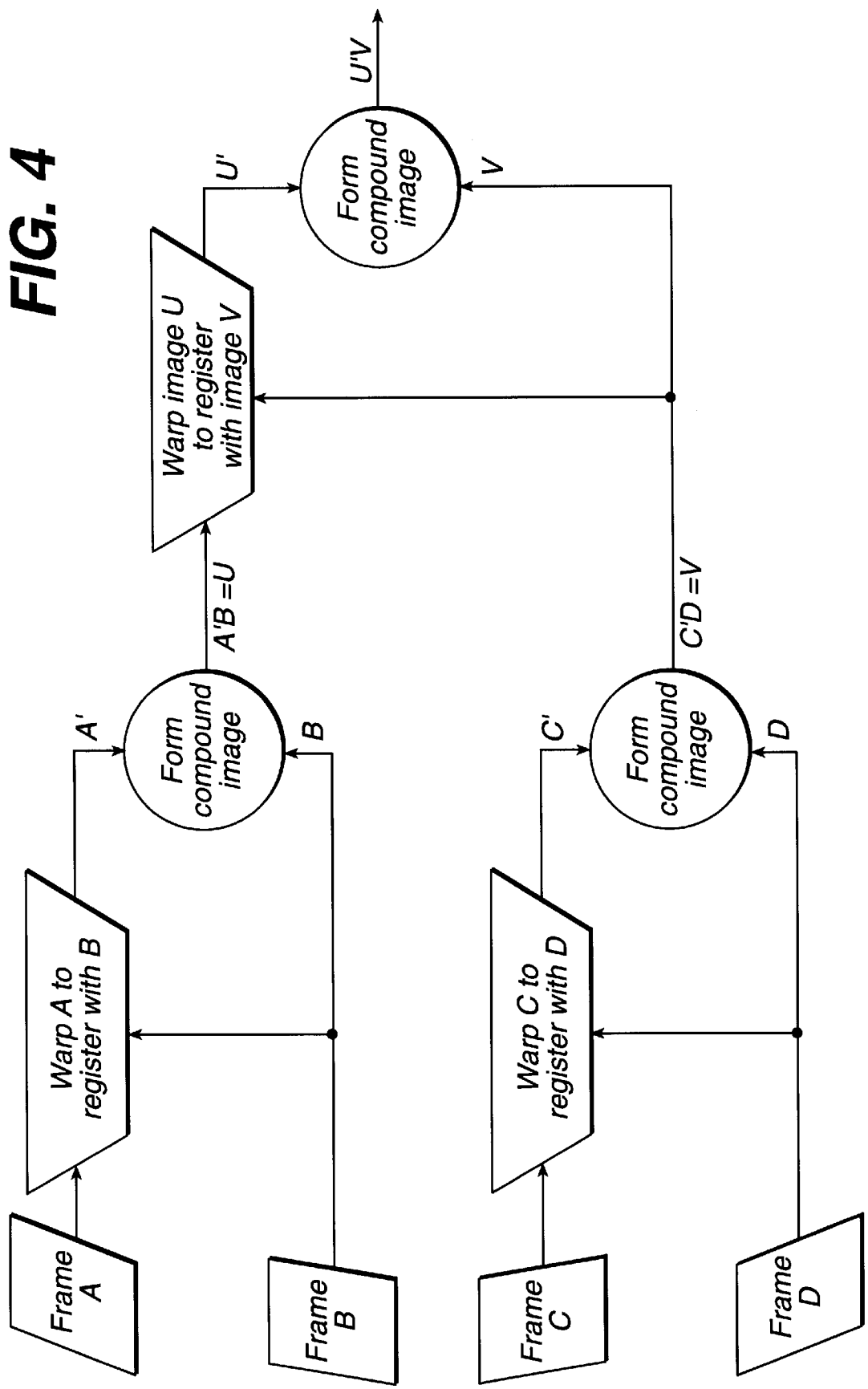
FIG. 4 illustrates a flowchart for pyramid registration of the constituent frames of a compound image.

FIG. 4 illustrates a second embodiment in which pairs of images are registered and compounded, followed by a second step of registration and compounding of the previously registered and compounded pairs, termed herein as the "pyramid" method. FIG. 4 illustrates the pyramid technique for four component images A, B, C, and D. In the first step of the method the A and B frames are registered and compounded, then the C and D frames are registered and compounded. These intermediate compounded images, identified as U and V, are then registered and compounded to form the final compound image.

If only partial correction of the misregistration error is acceptable (or if conditions exist where registration of all component frames may be unreliable), then the first registration step can be omitted, gaining a substantial reduction in computational requirements. In that case the temporally adjacent images A and B are compounded, as are temporally adjacent images C and D. The resulting two intermediate compounded images, U and V, are then registered and compounded. Another alternative is to register frames A and B and then frames C and D, compound the registered frame pairs, then omit the last registration step and simply compound the intermediate U and V images to form the final compound image.

Figure 7:
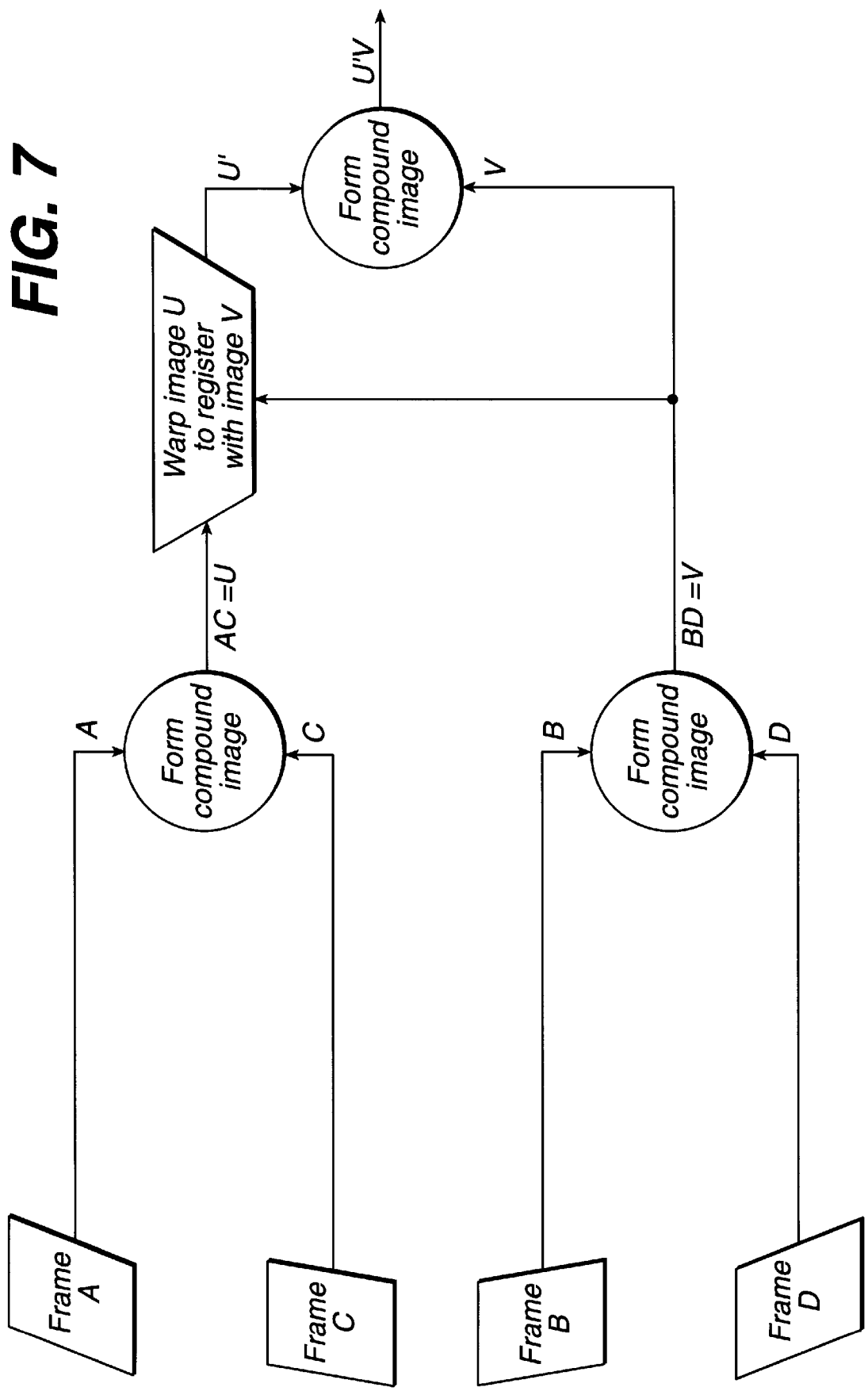
FIG. 7 illustrates a flowchart for the successive registration and compounding of new component frames in conjunction with the removal of old component frames from the compound image.

FIG. 7 illustrates a further aspect of the present invention which is that, while the A,C,B,D frame sequence in this drawing is temporally sequential, the temporally adjacent frames are not spatially adjacent. That is, the look direction of frame C is not the angularly similar look direction of frame B, but is at a significantly different look direction from that of frame A, the frame with which it is initially compounded. The same is true of the B and D frame pair. This will result in the best possible intermediate compounded images U and V, since the temporal adjacency will reduce motion artifacts while the more greatly divergent look directions will reduce the anisotropy in the compounded image.

Figure 5:
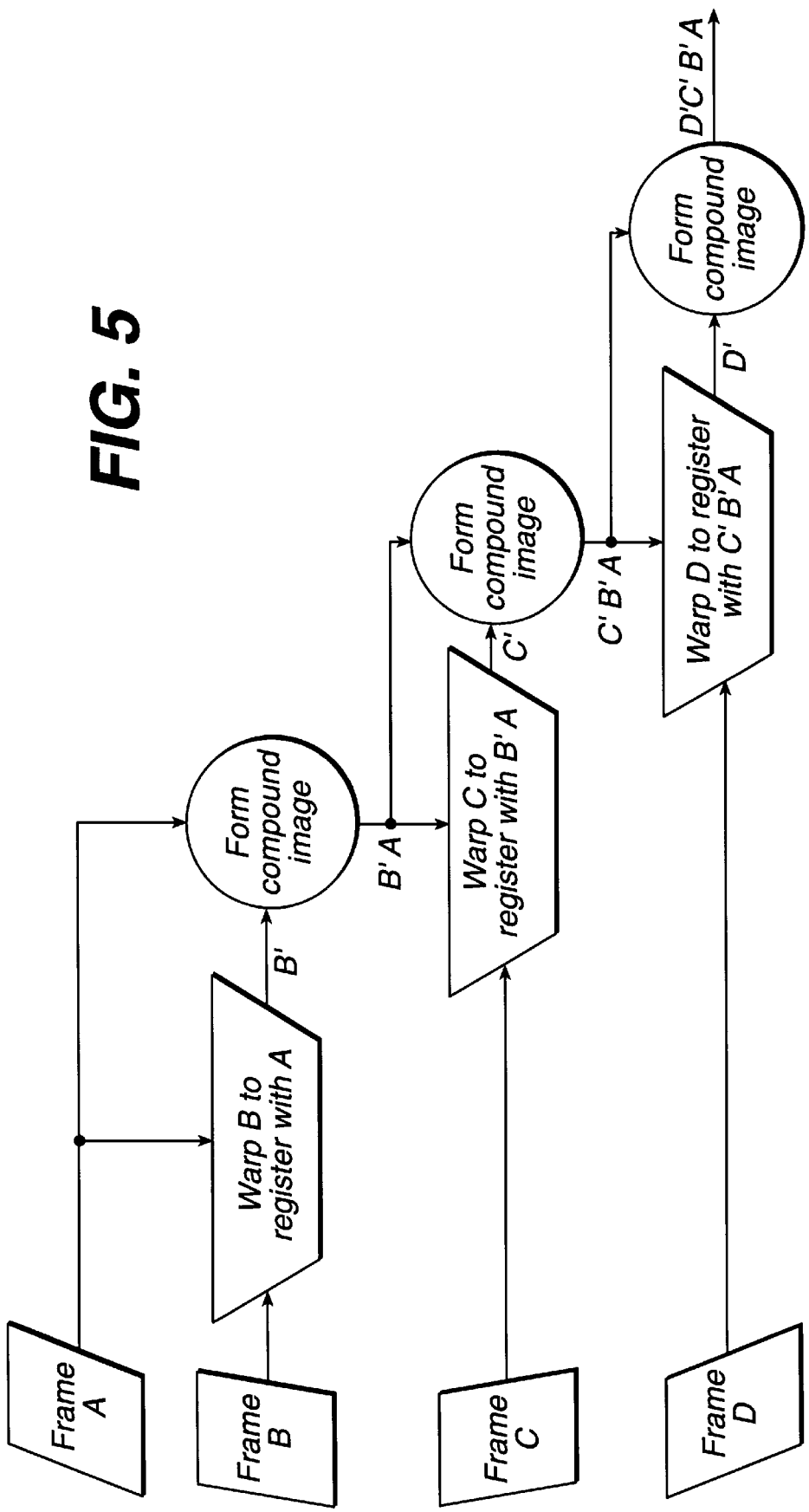
FIG. 5 illustrates a flowchart for the successive registration and compounding of the constituent frames of a compound image.

FIG. 5 shows yet another embodiment where the compound image is accumulated frame by frame with successive registration and compounding steps. In the illustrated embodiment images A and B are registered and compounded to form a first intermediate compound image B'. Image B' is then registered and compounded with image C to form a further intermediate compound image C'. Image C' is then registered and compounded with a further image D to form the final compound image.

Figure 6:
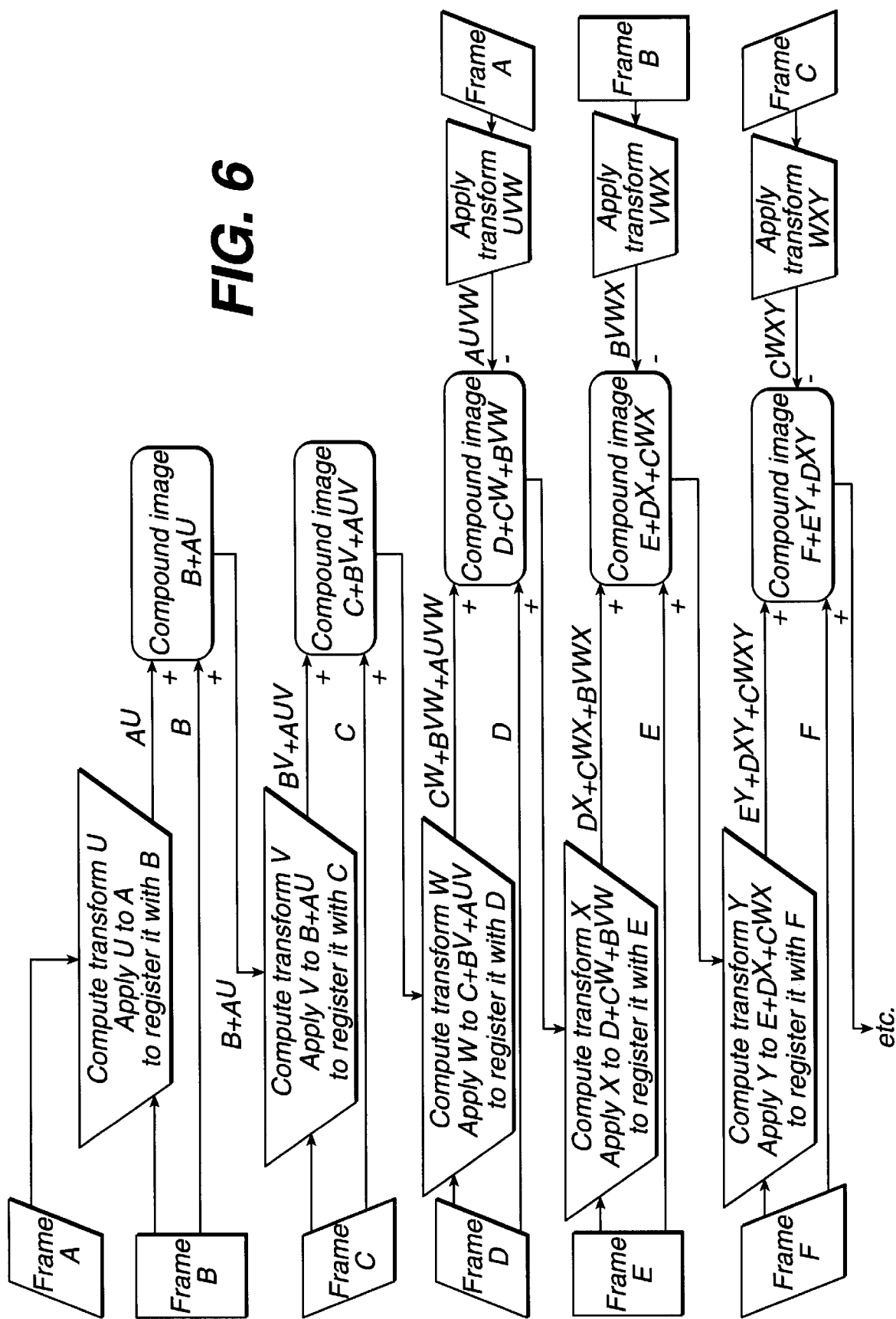
FIG. 6 illustrates a flowchart for pyramidal registration of non-sequential image frames to form a compound image.

FIG. 6 illustrates yet another embodiment in which the registration transforms undergone by each component frame are tracked and stored, and used to completely remove the component frame when the compounded image is updated with a current component frame. At the top of the drawing the transform U necessary to register the estimates of frame A to those of frame B is computed and used to perform the registration of frame A to frame B, thus producing a two-frame compounded image $B+A^U$. Next, the transform V which registers the compounded image $B+A^U$ to frame C is computed and used to perform the registration, thereby producing a three-frame compounded image $C+B^V+A^{UV}$. Note that frame A has now been processed by transforms U and V. In this example a three-frame compounded image is the desired result, which means that as the next frame D is registered and combined with the compounded image, the initial frame A is removed from the combination. This involves two process steps. In one of the process steps, the transform W which registers the compounded image $C+B^V+A^{UV}$ to frame D is computed and used to perform the registration of the compounded image to frame D. In the other process step the transform UVW, representing the transforms previously experienced by frame A, are applied to frame A and subtracted from the compounded image. This removes all vestiges of frame A from the combination, since the transforms delineate the current locations of frame A data after all of the transformations undergone by the frame data. The frame A data is thus cleanly removed from the compounded image, leaving a new compounded image of the form $D+C^W+B^{VW}$. In the next step another new three-component compounded image, $E+D^X+C^{WX}$ is produced which includes data from frames C, D, and E after removal of frame B data by operation of the transform VWX, which tracks the changes experienced by previous registrations of frame B. It is seen that each subtraction cleanly removes the oldest component frame data by virtue of the use of the complete transform undergone by the oldest frame, and that a new compounded image for display is produced with the addition of each new component frame. This registration technique can advantageously be implemented with a single compound image accumulator, as more fully described in U.S. Pat. [appl. SN ATL-198] entitled "ULTRASONIC DIAGNOSTIC IMAGING SYSTEM WITH REAL TIME SPATIAL COMPOUNDING PROCESSOR."

The above embodiments of the present invention for conducting registration prior to compounding perform substantially equivalently as long as all the component frames have a high degree of similarity. In practice, however, the component frames do not always display the desired high degree of correlation due to "spatial artifacts" produced by non-uniform, anisotropic, or scattering properties of tissue such as:

1) highly attenuating tissues (e.g. fetal ribs, gall stones, certain types of tumors, etc.) can cause image artifacts called "acoustic shadows". These shadows are cast in a direction that depends on the angle of incidence of the ultrasound beam. A spatial compound image comprising component frames of different angles of incidence to the same target will contain acoustic shadows in different locations, reducing the correlation between the component frames. The apparent decorrelation due to acoustic shadowing cannot be corrected by image registration methods, since registration of the shadows would cause misregistration of the real anatomy.

2) anisotropic reflectors such as tendons, bony surfaces, and the walls of blood vessels reflect ultrasound in a specular, mirror-like manner, producing artifacts called "highlight echoes." Highlight echoes shift position depending on the angle of insonification, creating decorrelation and/or apparent misregistration between component frames. Although it is generally desirable to acquire spatially diverse views of such specular targets so that they appear more continuous in the compound image, the resulting decorrelation and/or misregistration due to highlight artifacts can confound image registration methods and produce inaccurate registration results.

3) unresolved scatterers within tissue often produce a "texture pattern" superimposed on the ultrasound image. Although some of this pattern may be due to underlying regular or semi-regular microstructure, much of it is an undesirable, random mottling of the image known as "speckle." When the same tissue is imaged from independent spatial directions, the random speckle patterns are also independent, creating decorrelation from frame to frame that can contribute to inaccurate registration results.

In the presence of these spatial artifacts, the methods for registration prior to compounding do not all perform equivalently. For example, the reference frame method shown in FIG. 3 may fail to perform reliably if the component frames are acquired from substantially different directions. The resulting artifacts from shadowing or specular reflectors may prevent accurate registration prior to compounding. In this case, the pyramid method shown in FIG. 4 may perform better by registering spatially adjacent frames (with higher correlation) prior to compounding, followed by registration of the intermediate compound images. Fortunately, spatial compounding tends to improve the quality of the intermediate compound image by both filling-in specular reflectors more completely and reducing speckle. This potentially improves the quality of registration of the intermediate compound images prior to combining them into a final registered, compound image.

Another significant source of frame to frame decorrelation is due to motion of the scanhead in the direction perpendicular to the image plane (elevation motion decorrelation). When the clinical operator is searching for abnormalities (i.e. in a "survey mode") the probe is typically moved fairly rapidly in the elevation direction in order to view as much tissue as possible as quickly as possible. The result of elevation motion decorrelation is that temporally sequential component frames become increasingly decorrelated as structures move out of the scan plan and their corresponding image features disappear. Again, the reference frame method shown in FIG. 3 may fail to perform reliably because elevation motion decorrelation over the entire acquisition sequence may prevent accurate registration prior to compounding. The pyramid method shown in FIG. 4 may perform better by registering temporally adjacent frames (with higher correlation) prior to compounding, followed by registration of the intermediate compound images.

Figure 8:
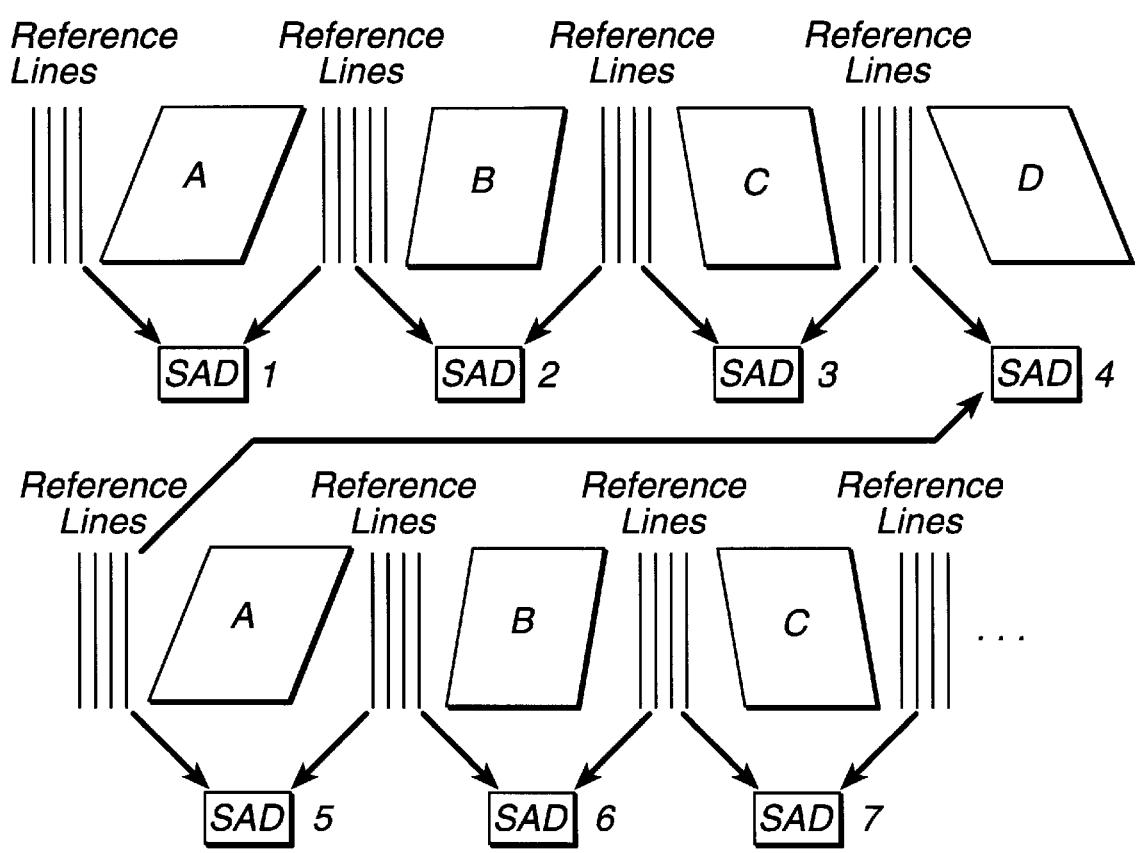
FIG. 8 illustrates the use of reference lines for image registration.

A preferred technique for sensing misregistration, shown in FIG. 8, is to acquire a small number of "calibration" lines interspersed between each component frame. The ROI defined by these calibration lines is preferably viewed from a constant look direction and is used for misregistration sensing using SAD or other algorithms. As FIG. 8 shows, the calibration or reference lines acquired between component frames are used to compute SAD or otherwise to measure the degree of misregistration that has occurred during the time required to acquire a component frame. The calibration lines need not be at a regular line density or uniform angularity, but may be widely spaced and/or scattered across the image plane, and may be differently angled. A sparsely sampled frame will perform admirably. Although the additional lines will lower the overall frame rate, the temporal degradation need not be very great due to the low number of reference lines and, in any case, an adaptive approach can still give the user the sense of a satisfactorily high frame rate.

What is claimed is:

1. A method for reducing blurring in spatially compounded ultrasonic diagnostic images comprising the steps of:

acquiring component ultrasonic diagnostic images at a plurality of different electronically steered look directions, said component images having a predetermined spatial relationship to each other in the absence of motion;

spatially registering said component images in consideration of the effects of motion prior to compounding; and spatially compounding said spatially registered component images to form a spatially compounded image.

2. The method of claim 1, wherein said step of spatially registering comprises spatially registering a component image frame with a compound image of registered component image frames.

3. The method of claim 2, wherein said step of spatially compounding comprises combining a component image frame with a compound image with which said component image frame has been spatially registered.

4. The method of claim 1, wherein said steps of registering and compounding component images occurs in the temporal sequence in which the images are acquired.

5. The method of claim 1, wherein said step of spatially registering comprises registering component image frames which are not temporally adjacent.

6. The method of claim 1, farther comprising the step of designating a component image frame as a reference image; and wherein said step of spatially registering comprises registering other component image frames with said reference image.

7. The method of claim 1, wherein said step of spatially registering comprises:

registering and combining component image frames to form intermediate compounded images; and wherein said step of spatially compounding comprises combining intermediate compounded images.

8. The method of claim 7 wherein said step of spatially compounding comprises registering and combining intermediate compounded images.

9. The method of claim 7, wherein said step of spatially registering comprises:

registering and combining pairs of component images which are not spatially adjacent to form intermediate compounded images.

10. The method of claim 1, wherein said step of spatially registering comprises:
   calculating a metric representing the similarity or difference between component image frames; and
   registering said component image frames on the basis of said metric.

11. The method of claim 10, further comprising the step of acquiring periodic calibration image data,
   wherein said metric is calculated on the basis of said calibration image data.

12. The method of claim 10, further comprising the step of:
   removing a previously compounded component image frame on the basis of a registration metric based upon said previously compounded component image frame.

13. The method of claim 10, wherein said step of calculating a metric calculates said metric for component image frames having corresponding look directions.

14. The method of claim 1, wherein said step of spatially registering comprises registering component image frames exhibiting look directions which are not spatially adjacent.

15. The method of claim 1, wherein said step of spatially registering comprises registering component image frames exhibiting look directions which are not temporally adjacent.

16. The method of claim 1, further comprising the step of:
   acquiring reference image data on a time interleaved basis with said component images; and
   wherein said step of spatially registering spatially registers component images on the basis of said reference image data.

17. The method of claim 16, wherein said reference image data comprises groups of reference lines acquired between the times of acquisition of component images.

18. The method of claim 17, wherein said reference lines exhibit a corresponding spatial alignment.

19. The method of claim 1, further comprising the steps of:
   acquiring a new component image; and
   spatially registering said new component image and said spatially compounded image; and
   spatially compounding said new component image with said spatially compounded image and removing a component image previously included in said spatially compounded image.

* * * * *